US009890348B2

(12) United States Patent
Cohen et al.

(10) Patent No.: US 9,890,348 B2
(45) Date of Patent: Feb. 13, 2018

(54) NATURAL OIL METATHESIS COMPOSITIONS AND METHODS

(71) Applicant: ELEVANCE RENEWABLE SCIENCES, INC., Woodridge, IL (US)

(72) Inventors: Steven A. Cohen, Naperville, IL (US); M. Michelle Morie-Bebel, Naperville, IL (US); Alexander D. Ilseman, Chicago, IL (US); Benjamin Bergmann, Anderson, SC (US); Stephen A. DiBiase, River Forest, IL (US); S. Alexander Christensen, Northwoods, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 4 days.

(21) Appl. No.: 13/922,626

(22) Filed: Jun. 20, 2013

(65) Prior Publication Data
US 2013/0344012 A1    Dec. 26, 2013

Related U.S. Application Data

(60) Provisional application No. 61/662,318, filed on Jun. 20, 2012, provisional application No. 61/781,892, filed on Mar. 14, 2013.

(51) Int. Cl.
| *C11C 3/00* | (2006.01) |
| *C10G 3/00* | (2006.01) |
| *A61K 8/37* | (2006.01) |
| *A61K 8/49* | (2006.01) |
| *A61Q 19/10* | (2006.01) |
| *C11B 3/00* | (2006.01) |
| *C11C 3/10* | (2006.01) |

(52) U.S. Cl.
CPC .............. *C11C 3/00* (2013.01); *A61K 8/375* (2013.01); *A61K 8/4973* (2013.01); *A61Q 19/10* (2013.01); *C10G 3/42* (2013.01); *C11B 3/008* (2013.01); *C11C 3/10* (2013.01); *A61K 2800/10* (2013.01); *Y02P 30/20* (2015.11)

(58) Field of Classification Search
None
See application file for complete search history.

(56) References Cited

U.S. PATENT DOCUMENTS

| 2,619,422 | A | 11/1952 | Diamond |
| 3,448,178 | A | 6/1969 | Flanagan |
| 3,896,053 | A | 7/1975 | Broecker et al. |
| 5,142,072 | A | 8/1992 | Stipp et al. |
| 5,506,363 | A | 4/1996 | Grate et al. |
| 5,700,516 | A | 12/1997 | Sandvick et al. |
| 5,734,070 | A | 3/1998 | Tacke et al. |
| 6,197,894 | B1 | 3/2001 | Sunaga et al. |
| 6,211,315 | B1 | 4/2001 | Larock et al. |
| 6,486,264 | B1 | 11/2002 | Tsunogae et al. |
| 6,696,597 | B2 | 2/2004 | Pedersen et al. |
| 6,900,347 | B2 | 5/2005 | Paulson et al. |
| 6,962,729 | B2 | 11/2005 | Tokas et al. |
| 6,987,154 | B2 | 1/2006 | Choi et al. |
| 7,026,495 | B1 | 4/2006 | Pedersen et al. |
| 7,119,216 | B2 | 10/2006 | Newman et al. |
| 7,176,336 | B2 | 2/2007 | Maughon et al. |
| 7,314,904 | B2 | 1/2008 | Nadolsky et al. |
| 7,365,140 | B2 | 4/2008 | Piers et al. |
| 7,576,227 | B2 | 8/2009 | Lysenko |
| 7,585,990 | B2 | 9/2009 | Toor et al. |
| 7,678,932 | B2 | 3/2010 | Thurier et al. |
| 7,812,185 | B2 | 10/2010 | Burdett et al. |
| 2002/0095007 | A1 | 7/2002 | Larock et al. |
| 2005/0027136 | A1 | 2/2005 | Toor et al. |
| 2005/0070750 | A1 | 3/2005 | Newman et al. |
| 2005/0203324 | A1 | 9/2005 | Lee et al. |
| 2006/0079704 | A1 | 4/2006 | Lacombe et al. |
| 2006/0289138 | A1 | 12/2006 | Borsinger et al. |
| 2007/0179307 | A1 | 8/2007 | Olivier-Bourbigou et al. |
| 2007/0270621 | A1 | 11/2007 | Millis et al. |
| 2008/0027194 | A1 | 1/2008 | Schrodi |

(Continued)

FOREIGN PATENT DOCUMENTS

| EP | 0429995 A2 | 6/1991 |
| EP | 1408064 A1 | 4/2004 |

(Continued)

OTHER PUBLICATIONS

Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.
Baumann et al., "Natural Fats and Oils—Renewable Raw Materials for the Chemical Industry," Angewandte Chemie International Edition in English, vol. 27, 1988, pp. 41-62.
Biermann et al., "New Syntheses with Oils and Fats as Renewable Raw Materials for the Chemical Industry,", Angewandte Chemie International Edition, vol. 39, 2000, pp. 2206-2224.
Boelhouwer et al., "Metathesis Reactions of Fatty Acid Esters," Progress of Lipid Research, Pergamon Press, vol. 24, No. 3, 1985, pp. 243-267.

(Continued)

Primary Examiner — Mina Haghighatian
Assistant Examiner — Luke Karpinski
(74) Attorney, Agent, or Firm — Kilpatrick Townsend & Stockton LLP

(57) ABSTRACT

A metathesized natural oil composition comprising (i) a mixture olefins and/or esters, or (ii) a metathesized natural oil, is disclosed. The metathesized natural oil composition has a number average molecular weight in the range from about 100 g/mol to about 150,000 g/mol, a weight average molecular weight in the range from about 1,000 g/mol to about 100,000 g/mol, a z-average molecular weight in the range from about 5,000 g/mol to about 1,000,000 g/mol, and a polydispersity index of about 1 to about 20. The metathesized natural oil composition is metathesized at least once.

3 Claims, 5 Drawing Sheets

(56) References Cited

U.S. PATENT DOCUMENTS

| | | |
|---|---|---|
| 2008/0064891 A1 | 3/2008 | Lee |
| 2009/0048459 A1 | 2/2009 | Tupy et al. |
| 2009/0126602 A1 | 5/2009 | Murphy et al. |
| 2009/0217568 A1 | 9/2009 | Murphy et al. |
| 2009/0220443 A1 | 9/2009 | Braksmayer et al. |
| 2009/0259065 A1 | 10/2009 | Abraham et al. |
| 2009/0264672 A1 | 10/2009 | Abraham et al. |
| 2010/0047499 A1 | 2/2010 | Braksmayer et al. |
| 2010/0094034 A1 | 4/2010 | Kaido et al. |
| 2010/0145086 A1 | 6/2010 | Schrodi et al. |
| 2013/0281551 A1* | 10/2013 | Stella .................. A61Q 19/00 514/785 |

FOREIGN PATENT DOCUMENTS

| | | |
|---|---|---|
| EP | 1810960 A1 | 7/2007 |
| FR | 2878246 A1 | 5/2006 |
| JP | 56-077243 A | 6/1981 |
| JP | S56104847 | 8/1981 |
| JP | 09-014574 A | 1/1997 |
| SU | 1565872 A1 | 7/1988 |
| WO | WO 94/23836 A1 | 10/1994 |
| WO | WO 96/04289 A1 | 2/1996 |
| WO | WO 01/36368 A2 | 5/2001 |
| WO | WO 03/057983 A1 | 7/2003 |
| WO | WO 03/093215 A1 | 11/2003 |
| WO | WO 03/104348 A1 | 12/2003 |
| WO | WO 2004/033388 A1 | 4/2004 |
| WO | WO 2004/062763 A2 | 7/2004 |
| WO | WO 2005/080455 A1 | 9/2005 |
| WO | WO 2006/052688 A2 | 5/2006 |
| WO | WO 2007/081987 A2 | 7/2007 |
| WO | WO 2007/103398 A1 | 9/2007 |
| WO | WO 2007/103460 A2 | 9/2007 |
| WO | WO 2008/008420 A1 | 1/2008 |
| WO | WO 2008/010961 A2 | 1/2008 |
| WO | WO 2008/048520 A2 | 4/2008 |
| WO | WO 2008/063322 A2 | 5/2008 |
| WO | WO 2008/140468 A2 | 11/2008 |
| WO | WO 2010/062958 A1 | 6/2010 |
| WO | WO 2011/046872 A2 | 4/2011 |
| WO | WO 2012/006324 A1 | 1/2012 |

OTHER PUBLICATIONS

Chatterjee et al., "Synthesis of Trisubstituted Alkenes via Olefin Cross-Metathesis," Organic Letters, vol. 1, No. 11, 1999, pp. 1751-1753.

Choi et al., "Olefin Metathesis Involving Ruthenium Enoic Carbene Complexes," Journal of the American Chemical Society, vol. 123, No. 42, 2001, pp. 10417-10418.

Connon et al., "A Solid-Supported Phosphine-Free Ruthenium Alkylidene for Olefin Metathesis in Methanol and Water," Bioorganic & Medical Chem Letters, vol. 12, No. 14, 2002, pp. 1873-1876.

Delaude et al., Metathesis, Kirk-Othmer Encyclopedia of Chemical Technology, Dec. 2005, vol. 26, pp. 920-958.

Dunne et al., "A Highly Efficient Olefin Metathesis Initiator: Improved Synthesis and Reactivity Studies," Tetrahedron Letters, vol. 44, No. 13, 2003, pp. 2733-2736.

Erhan et al. , "Drying Properties of Metathesized Soybean Oil," Journal of American Oil Chemists' Society, AOCS Press, vol. 74, No. 6, 1997, pp. 703-706.

Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.

Maynard et al., "Purification Technique for the Removal of Ruthenium from Olefin Metathesis Reaction Products," Tetrahedron Letters, vol. 40, No. 22, 1999, pp. 4137-4140.

Mol, "Applications of Olefin Metathesis in Oleochemistry: An Example of Green Chemistry," Green Chemistry, Royal Society of Chemistry, Cambridge, GB, vol. 4, 2002, pp. 5-13.

Mol et al., "Metathesis in Oleochemistry," J Braz Chem Soc, vol. 9, No. 1, 1998, pp. 1-11.

Mol, "Catalytic Metathesis of Unsaturated Fatty Acid Esters and Oils," Topics in Catalysis, vol. 27, No. 1-4, 2004, pp. 97-104.

Ngo et al., Methathesis of Unsaturated Fatty Acids: Synthesis of Long-Chain Unsaturated-[alpha],[omega]-Dicarboxylic Acids, Journal of the American Oil Chemists, Jul. 2006, vol. 83m Issue 7, p. 629, 9 pgs.

Patel, Jim et al., "Cross-metathesis of unsaturated natural oils with 2-butene, High conversion and productive catalyst turnovers," Chem. Commun., 2005, pp. 5546-5547.

Patel et al., "High conversion and productive catalyst turnovers in cross-metathesis reactions of natural oils with 2-butene", Green Chemistry, 2006, vol. 8, pp. 450-454.

Refvik et al., "Ruthenium-Catalyzed Metathesis of Vegetable Oils," Journal of American Oil Chemists' Society, AOCS Press, vol. 76, No. 1, 1999, pp. 93-98.

Refvik, M.D. et al., "The Chemistry of Metathesized Soybean Oil," JAOCS, vol. 76, No. 1, 1999, pp. 99-102.

Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.

Tian et al., "Model Studies and the ADMET Polymerization of Soybean Oil," Journal of American Oil Chemists' Society, AOCS Press, vol. 79, No. 5, 2002, pp. 479-488.

Warwel, Siegfried et al., "Synthesis of Dicarboxylic Acids by Transition-Metal Catalyzed Oxidative Cleavage of Terminal-Unsaturated Fatty Acids," Topics in Current Chemistry, vol. 164, 1993, 20 pages.

International Preliminary Report on Patentability and Written Opinion of the International Searching Authority issued in PCT Patent Application No. PCT/US2013/046735, dated Dec. 31, 2014, 7 pages.

International Search Report issued in PCT Patent Application No. PCT/US2013/046735, dated Sep. 18, 2013, 3 pages.

* cited by examiner

NATURAL OIL METATHESIS COMPOSITIONS AND METHODS

CROSS-REFERENCE TO RELATED APPLICATIONS

A claim of priority for this application under 35 U.S.C. § 119(e) is hereby made to U.S. Provisional Patent Application No. 61/662,318, filed Jun. 20, 2012 and U.S. Provisional Patent Application No. 61/781,892, filed Mar. 14, 2013; the disclosures of which are incorporated herein by reference in their entireties.

BACKGROUND

In recent years, there has been an increased demand for environmentally friendly techniques for manufacturing materials typically derived from petroleum sources. In view of the non-renewable nature of petroleum, it is highly desirable to provide non-petroleum alternatives for material manufacturing biofuels, waxes, plastics, cosmetics, personal care items, and the like. One of the methods to manufacture such materials is through generating compositions through the metathesis of natural oil feedstocks, such as vegetable and seed-based oils.

DETAILED DESCRIPTION

Figure 1:
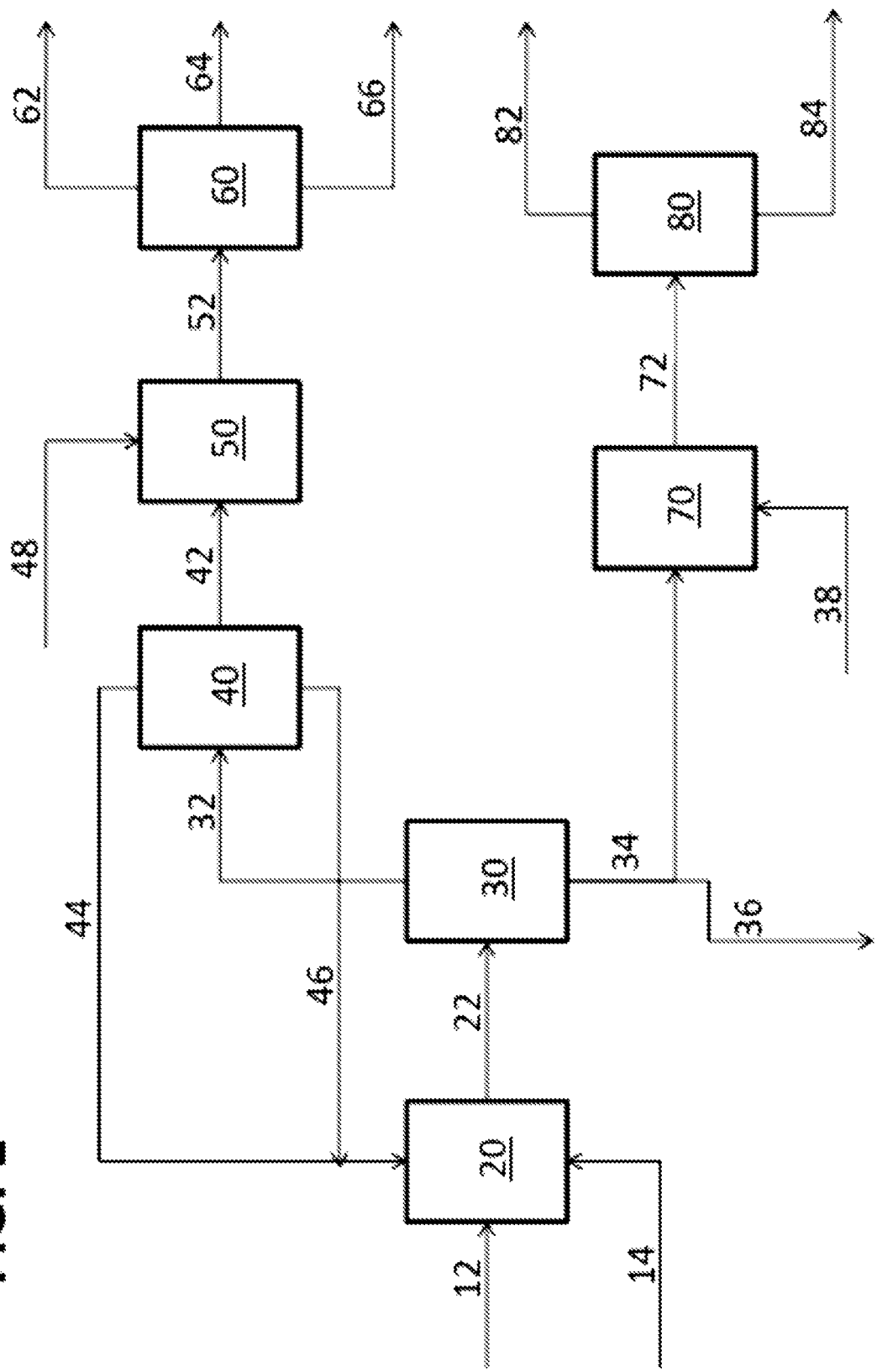
FIG. 1 depicts a schematic diagram of a process to produce a metathesized natural oil product and a transesterified product from a natural oil.

It is to be understood that unless specifically stated otherwise, references to "a," "an," and/or "the" may include one or more than one, and that reference to an item in the singular may also include the item in the plural.

The terms "natural oils," "natural feedstocks," or "natural oil feedstocks" may refer to oils derived from plants or animal sources. The term "natural oil" includes natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

The term "natural oil derivatives" refers to derivatives thereof derived from natural oil. The methods used to form these natural oil derivatives may include one or more of addition, neutralization, overbasing, saponification, transesterification, esterification, amidification, hydrogenation, isomerization, oxidation, alkylation, acylation, sulfurization, sulfonation, rearrangement, reduction, fermentation, pyrolysis, hydrolysis, liquefaction, anaerobic digestion, hydrothermal processing, gasification or a combination of two or more thereof. Examples of natural derivatives thereof may include carboxylic acids, gums, phospholipids, soapstock, acidulated soapstock, distillate or distillate sludge, fatty acids, fatty acid esters, as well as hydroxy substituted variations thereof, including unsaturated polyol esters. In some embodiments, the natural oil derivative may comprise an unsaturated carboxylic acid having from about 5 to about 30 carbon atoms, having one or more carbon-carbon double bonds in the hydrocarbon (alkene) chain. The natural oil derivative may also comprise an unsaturated fatty acid alkyl (e.g., methyl) ester derived from a glyceride of natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil).

The term "low-molecular-weight olefin" may refer to any one or combination of unsaturated straight, branched, or cyclic hydrocarbons in the $C_2$ to $C_{14}$ range. Low-molecular-weight olefins include "alpha-olefins" or "terminal olefins," wherein the unsaturated carbon-carbon bond is present at one end of the compound. Low-molecular-weight olefins may also include dienes or trienes. Examples of low-molecular-weight olefins in the $C_2$ to $C_6$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Other possible low-molecular-weight olefins include styrene and vinyl cyclohexane. In certain embodiments, it is preferable to use a mixture of olefins, the mixture comprising linear and branched low-molecular-weight olefins in the $C_4$-$C_{10}$ range. In one embodiment, it may be preferable to use a mixture of linear and branched $C_4$ olefins (i.e., combinations of: 1-butene, 2-butene, and/or isobutene). In other embodiments, a higher range of $C_{11}$-$C_{14}$ may be used.

The term "metathesis monomer" refers to a single entity that is the product of a metathesis reaction which comprises a molecule of a compound with one or more carbon-carbon double bonds which has undergone an alkylidene unit interchange via one or more of the carbon-carbon double bonds either within the same molecule (intramolecular metathesis) and/or with a molecule of another compound containing one or more carbon-carbon double bonds such as an olefin (intermolecular metathesis).

The term "metathesis dimer" refers to the product of a metathesis reaction wherein two reactant compounds, which can be the same or different and each with one or more carbon-carbon double bonds, are bonded together via one or more of the carbon-carbon double bonds in each of the reactant compounds as a result of the metathesis reaction.

The term "metathesis trimer" refers to the product of one or more metathesis reactions wherein three molecules of two or more reactant compounds, which can be the same or different and each with one or more carbon-carbon double bonds, are bonded together via one or more of the carbon-carbon double bonds in each of the reactant compounds as a result of the one or more metathesis reactions, the trimer containing three bonded groups derived from the reactant compounds.

The term "metathesis tetramer" refers to the product of one or more metathesis reactions wherein four molecules of two or more reactant compounds, which can be the same or different and each with one or more carbon-carbon double bonds, are bonded together via one or more of the carbon-carbon double bonds in each of the reactant compounds as a result of the one or more metathesis reactions, the tetramer containing four bonded groups derived from the reactant compounds.

The term "metathesis pentamer" refers to the product of one or more metathesis reactions wherein five molecules of two or more reactant compounds, which can be the same or different and each with one or more carbon-carbon double bonds, are bonded together via one or more of the carbon-carbon double bonds in each of the reactant compounds as a result of the one or more metathesis reactions, the pentamer containing five bonded groups derived from the reactant compounds.

The term "metathesis hexamer" refers to the product of one or more metathesis reactions wherein six molecules of two or more reactant compounds, which can be the same or different and each with one or more carbon-carbon double bonds, are bonded together via one or more of the carbon-carbon double bonds in each of the reactant compounds as a result of the one or more metathesis reactions, the hexamer containing six bonded groups derived from the reactant compounds.

The term "metathesis heptamer" refers to the product of one or more metathesis reactions wherein seven molecules of two or more reactant compounds, which can be the same or different and each with one or more carbon-carbon double bonds, are bonded together via one or more of the carbon-carbon double bonds in each of the reactant compounds as a result of the one or more metathesis reactions, the heptamer containing seven bonded groups derived from the reactant compounds.

The term "metathesis octamer" refers to the product of one or more metathesis reactions wherein eight molecules of two or more reactant compounds, which can be the same or different and each with one or more carbon-carbon double bonds, are bonded together via one or more of the carbon-carbon double bonds in each of the reactant compounds as a result of the one or more metathesis reactions, the octamer containing eight bonded groups derived from the reactant compounds.

The term "metathesis nonamer" refers to the product of one or more metathesis reactions wherein nine molecules of two or more reactant compounds, which can be the same or different and each with one or more carbon-carbon double bonds, are bonded together via one or more of the carbon-carbon double bonds in each of the reactant compounds as a result of the one or more metathesis reactions, the nonamer containing nine bonded groups derived from the reactant compounds.

The term "metathesis decamer" refers to the product of one or more metathesis reactions wherein ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the decamer containing ten bonded groups derived from the reactant compounds.

The term "metathesis oligomer" refers to the product of one or more metathesis reactions wherein two or more molecules (e.g., 2 to about 10, or 2 to about 4) of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing a few (e.g., 2 to about 10, or 2 to about 4) bonded groups derived from the reactant compounds. In some embodiments, the term "metathesis oligomer" may include metathesis reactions wherein greater than ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing greater than ten bonded groups derived from the reactant compounds.

As used herein, the terms "metathesize" and "metathesizing" may refer to the reacting of a natural oil feedstock in the presence of a metathesis catalyst to form a metathesized natural oil product comprising a new olefinic compound and/or esters. Metathesizing may refer to cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming an oligomer having a new mixture of olefins and esters that may comprise one or more of: metathesis monomers, metathesis dimers, metathesis trimers, metathesis tetramers, metathesis pentamers, and higher order metathesis oligomers (e.g., metathesis hexamers, metathesis, metathesis heptamers, metathesis octamers, metathesis nonamers, metathesis decamers, and higher than metathesis decamers and above).

Metathesis is a catalytic reaction generally known in the art that involves the interchange of alkylidene units among compounds containing one or more double bonds (e.g., olefinic compounds) via the formation and cleavage of the carbon-carbon double bonds. Metathesis may occur between two like molecules (often referred to as self-metathesis) and/or it may occur between two different molecules (often referred to as cross-metathesis). Self-metathesis may be represented schematically as shown in Equation A below.

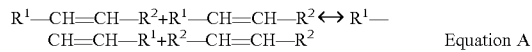

$$R^1\text{—CH}=\text{CH—}R^2 + R^1\text{—CH}=\text{CH—}R^2 \leftrightarrow R^1\text{—CH}=\text{CH—}R^1 + R^2\text{—CH}=\text{CH—}R^2 \quad \text{Equation A}$$

wherein $R^1$ and $R^2$ are organic groups.

Cross-metathesis may be represented schematically as shown in Equation B below.

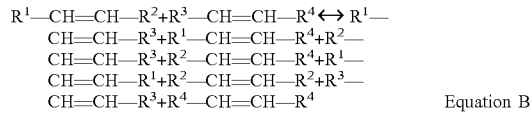

$$R^1\text{—CH}=\text{CH—}R^2 + R^3\text{—CH}=\text{CH—}R^4 \leftrightarrow R^1\text{—CH}=\text{CH—}R^3 + R^1\text{—CH}=\text{CH—}R^4 + R^2\text{—CH}=\text{CH—}R^3 + R^2\text{—CH}=\text{CH—}R^4 + R^1\text{—CH}=\text{CH—}R^1 + R^2\text{—CH}=\text{CH—}R^2 + R^3\text{—CH}=\text{CH—}R^3 + R^4\text{—CH}=\text{CH—}R^4 \quad \text{Equation B}$$

wherein $R^1$, $R^2$, $R^3$, and $R^4$ are organic groups.

The metathesis reaction of the natural oil feedstock having polyol esters (of fatty acids) results in the oligomerization of the natural oil feedstock having a mixture of olefins and esters that may comprise one or more of: metathesis monomers, metathesis dimers, metathesis trimers, metathesis tetramers, metathesis pentamers, and higher order metathesis oligomers (e.g., metathesis hexamers, metathesis heptamers, metathesis octamers, metathesis nonamers, metathesis decamers, and higher than metathesis decamers).

Natural oils of the type described herein typically are composed of triglycerides of fatty acids. These fatty acids may be either saturated, monounsaturated or polyunsaturated and contain varying chain lengths ranging from $C_8$ to $C_{30}$. The most common fatty acids include saturated fatty acids such as lauric acid (dodecanoic acid), myristic acid (tetradecanoic acid), palmitic acid (hexadecanoic acid), stearic acid (octadecanoic acid), arachidic acid (eicosanoic acid), and lignoceric acid (tetracosanoic acid); unsaturated acids include such fatty acids as palmitoleic (a C16 acid), and oleic acid (a C18 acid); polyunsaturated acids include such fatty acids as linoleic acid (a di-unsaturated C18 acid), linolenic acid (a tri-unsaturated C18 acid), and arachidonic acid (a tetra-unsubstituted C20 acid). The natural oils are further comprised of esters of these fatty acids in random placement onto the three sites of the trifunctional glycerine molecule. Different natural oils will have different ratios of these fatty acids, and within a given natural oil there is a range of these acids as well depending on such factors as where a vegetable or crop is grown, maturity of the vegetable or crop, the weather during the growing season, etc. Thus, it is difficult to have a specific or unique structure for any given natural oil, but rather a structure is typically based on some statistical average. For example soybean oil contains a mixture of stearic acid, oleic acid, linoleic acid, and linolenic acid in the ratio of 15:24:50:11, and an average number of double bonds of 4.4-4.7 per triglyceride. One method of quantifying the number of double bonds is the iodine value (IV) which is defined as the number of grams of iodine that will react with 100 grams of vegetable oil. Therefore for soybean oil, the average iodine value range is from 120-140. Soybean oil may comprises about 95% by weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

When a polyol ester comprises molecules having more than one carbon-carbon double bond, self-metathesis may result in oligomerization or polymerization of the unsaturates in the starting material. For example, Equation C depicts metathesis oligomerization of a representative species (e.g., a polyol ester) having more than one carbon-carbon double bond. In Equation C, the self-metathesis reaction results in the formation of metathesis dimers, metathesis trimers, and metathesis tetramers. Although not shown, higher order oligomers such as metathesis pentamers, hexamers, heptamers, octamers, nonamers, decamers, and higher than decamers, and mixtures of two or more thereof, may also be formed. The number of metathesis repeating units or groups in the metathesized natural oil may range from 1 to about 100, or from 2 to about 50, or from 2 to about 30, or from 2 to about 10, or from 2 to about 4. The molecular weight of the metathesis dimer may be greater than the molecular weight of the unsaturated polyol ester from which the dimer is formed. Each of the bonded polyol ester molecules may be referred to as a "repeating unit or group." Typically, a metathesis trimer may be formed by the cross-metathesis of a metathesis dimer with an unsaturated polyol ester. Typically, a metathesis tetramer may be formed by the cross-metathesis of a metathesis trimer with an unsaturated polyol ester or formed by the cross-metathesis of two metathesis dimers.

Equation C

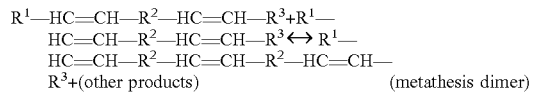

(metathesis dimer)

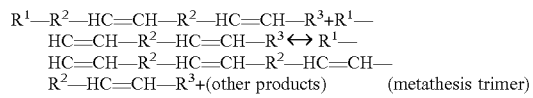

(metathesis trimer)

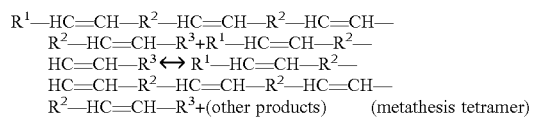

(metathesis tetramer)

where $R^1$, $R^2$, and $R^3$ are organic groups.

As noted, the self-metathesis of the natural oil occurs in the presence of a metathesis catalyst. As stated previously, the term "metathesis catalyst" includes any catalyst or catalyst system that catalyzes a metathesis reaction. Any known metathesis catalyst may be used, alone or in combination with one or more additional catalysts. Suitable homogeneous metathesis catalysts include combinations of a transition metal halide or oxo-halide (e.g., $WOCl_4$ or $WCl_6$) with an alkylating cocatalyst (e.g., $Me_4Sn$), or alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

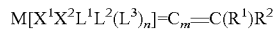

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086, the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

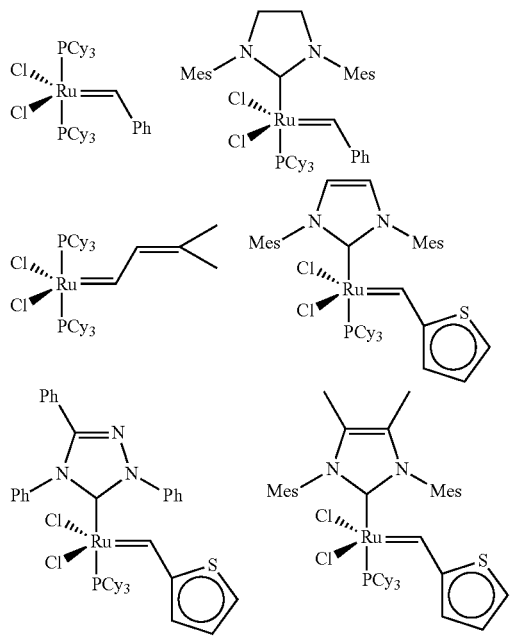

Heterogeneous catalysts suitable for use in the self- or cross-metathesis reaction include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. Nos. 4,545,941, 5,312,940, 5,342,909, 5,710,298, 5,728,785, 5,728,917, 5,750,815, 5,831,108, 5,922,863, 6,306,988, 6,414,097, 6,696,597, 6,794,534, 7,102,047, 7,378,528, and U.S. Pat. Appl. Publ. No. 2009/0264672 A1, and PCT/US2008/009635, pp. 18-47, all of which are incorporated herein by reference. A number of metathesis catalysts that may be advantageously employed in metathesis reactions are manufactured and sold by Materia, Inc. (Pasadena, Calif.).

A process for metathesizing a natural oil and treating the resulting metathesized natural oil is illustrated in FIG. 1. In certain embodiments, prior to the metathesis reaction, a natural oil feedstock may be treated to render the natural oil more suitable for the subsequent metathesis reaction. In one embodiment, the treatment of the natural oil involves the removal of catalyst poisons, such as peroxides, which may potentially diminish the activity of the metathesis catalyst. Non-limiting examples of natural oil feedstock treatment methods to diminish catalyst poisons include those described in PCT/US2008/09604, PCT/US2008/09635, and U.S. patent application Ser. Nos. 12/672,651 and 12/672,652, herein incorporated by reference in their entireties. In certain embodiments, the natural oil feedstock is thermally treated by heating the feedstock to a temperature greater than 100° C. in the absence of oxygen and held at the temperature for a time sufficient to diminish catalyst poisons in the feedstock. In other embodiments, the temperature is between approximately 100° C. and 300° C., between approximately 120° C. and 250° C., between approximately 150° C. and 210° C., or approximately between 190 and 200° C. In one embodiment, the absence of oxygen is achieved by sparging the natural oil feedstock with nitrogen, wherein the nitrogen gas is pumped into the feedstock treatment vessel at a pressure of approximately 10 atm (150 psig).

In certain embodiments, the natural oil feedstock is chemically treated under conditions sufficient to diminish the catalyst poisons in the feedstock through a chemical reaction of the catalyst poisons. In certain embodiments, the feedstock is treated with a reducing agent or a cation-inorganic base composition. Non-limiting examples of reducing agents include bisulfate, borohydride, phosphine, thiosulfate, and combinations thereof.

In certain embodiments, the natural oil feedstock is treated with an adsorbent to remove catalyst poisons. In one embodiment, the feedstock is treated with a combination of thermal and adsorbent methods. In another embodiment, the feedstock is treated with a combination of chemical and adsorbent methods. In another embodiment, the treatment involves a partial hydrogenation treatment to modify the natural oil feedstock's reactivity with the metathesis catalyst. Additional non-limiting examples of feedstock treatment are also described below when discussing the various metathesis catalysts.

Additionally, in certain embodiments, the low-molecular-weight olefin may also be treated prior to the metathesis reaction. Like the natural oil treatment, the low-molecular-weight olefin may be treated to remove poisons that may impact or diminish catalyst activity.

As shown in FIG. 1, after this optional treatment of the natural oil feedstock and/or low-molecular-weight olefin, the natural oil 12 is reacted with itself, or combined with a low-molecular-weight olefin 14 in a metathesis reactor 20 in the presence of a metathesis catalyst. In some embodiments, the natural oil 12 is soybean oil. Metathesis catalysts and metathesis reaction conditions are discussed in greater detail below. In certain embodiments, in the presence of a metathesis catalyst, the natural oil 12 undergoes a self-metathesis reaction with itself. In other embodiments, in the presence of the metathesis catalyst, the natural oil 12 undergoes a cross-metathesis reaction with the low-molecular-weight olefin 14. In certain embodiments, the natural oil 12 undergoes both self- and cross-metathesis reactions in parallel metathesis reactors. Multiple, parallel, or sequential metathesis reactions (at least one or more times) may be conducted. The self-metathesis and/or cross-metathesis reaction form a metathesized natural oil product 22 wherein the metathesized natural oil product 22 comprises olefins 32 and esters 34. In some embodiments, metathesized natural oil product 22 is metathesized soybean oil (MSBO). As used herein, "metathesized natural oil product" may also be referred to in the equivalent as "metathesized natural oil composition."

In certain embodiments, the low-molecular-weight olefin 14 is in the $C_2$ to $C_6$ range. As a non-limiting example, in one embodiment, the low-molecular-weight olefin 14 may comprise at least one of the following: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In another embodiment, the low-molecular-weight olefin 14 comprises at least one of styrene and vinyl cyclohexane. In another embodiment, the low-molecular-weight olefin 14 may comprise at least one of ethylene, propylene, 1-butene, 2-butene, and isobutene. In another embodiment, the low-molecular-weight olefin 14 comprises at least one alpha-olefin or terminal olefin in the $C_2$ to $C_{10}$ range.

In another embodiment, the low-molecular-weight olefin 14 comprises at least one branched low-molecular-weight olefin in the $C_4$ to $C_{10}$ range. Non-limiting examples of branched low-molecular-weight olefins include isobutene, 3-methyl-1-butene, 2-methyl-3-pentene, and 2,2-dimethyl-3-pentene. By using these branched low-molecular-weight olefins in the metathesis reaction, the methathesized natural oil product will include branched olefins, which can be subsequently hydrogenated to iso-paraffins. In certain embodiments, the branched low-molecular-weight olefins may help achieve the desired performance properties for a fuel composition, such as jet, kerosene, or diesel fuel.

As noted, it is possible to use a mixture of various linear or branched low-molecular-weight olefins in the reaction to achieve the desired metathesis product distribution. In one embodiment, a mixture of butenes (1-butene, 2-butenes, and, optionally, isobutene) may be employed as the low-molecular-weight olefin, offering a low cost, commercially available feedstock instead a purified source of one particular butene. Such low cost mixed butene feedstocks are typically diluted with n-butane and/or isobutane.

In certain embodiments, recycled streams from downstream separation units may be introduced to the metathesis reactor 20 in addition to the natural oil 12 and, in some embodiments, the low-molecular-weight olefin 14. For instance, in some embodiments, a $C_2$-$C_6$ recycle olefin stream or a $C_3$-$C_4$ bottoms stream from an overhead separation unit may be returned to the metathesis reactor. In one embodiment, as shown in FIG. 1, a light weight olefin stream 44 from an olefin separation unit 40 may be returned to the metathesis reactor 20. In another embodiment, the $C_3$-$C_4$ bottoms stream and the light weight olefin stream 44 are combined together and returned to the metathesis reactor 20. In another embodiment, a $C_{15+}$ bottoms stream 46 from the olefin separation unit 40 is returned to the metathesis reactor 20. In another embodiment, all of the aforementioned recycle streams are returned to the metathesis reactor 20.

The metathesis reaction in the metathesis reactor 20 produces a metathesized natural oil product 22. In one embodiment, the metathesized natural oil product 22 enters a flash vessel operated under temperature and pressure conditions which target $C_2$ or $C_2$-$C_3$ compounds to flash off and be removed overhead. The $C_2$ or $C_2$-$C_3$ light ends are comprised of a majority of hydrocarbon compounds having a carbon number of 2 or 3. In certain embodiments, the $C_2$ or $C_2$-$C_3$ light ends are then sent to an overhead separation unit, wherein the $C_2$ or $C_2$-$C_3$ compounds are further separated overhead from the heavier compounds that flashed off with the $C_2$-$C_3$ compounds. These heavier compounds are typically $C_3$-$C_5$ compounds carried overhead with the $C_2$ or $C_2$-$C_3$ compounds. After separation in the overhead separation unit, the overhead $C_2$ or $C_2$-$C_3$ stream may then be used as a fuel source. These hydrocarbons have their own value outside the scope of a fuel composition, and may be used or separated at this stage for other valued compositions and applications. In certain embodiments, the bottoms stream from the overhead separation unit containing mostly $C_3$-$C_5$ compounds is returned as a recycle stream to the metathesis reactor. In the flash vessel, the metathesized natural oil product 22 that does not flash overhead is sent downstream for separation in a separation unit 30, such as a distillation column.

Prior to the separation unit 30, in certain embodiments, the metathesized natural oil product 22 may be introduced to an adsorbent bed to facilitate the separation of the metathesized natural oil product 22 from the metathesis catalyst. In one embodiment, the adsorbent is a clay bed. The clay bed will adsorb the metathesis catalyst, and after a filtration step, the metathesized natural oil product 22 can be sent to the separation unit 30 for further processing. Separation unit 30 may comprise a distillation unit. In some embodiments, the distillation may be conducted, for example, by steam stripping the metathesized natural oil product. Distilling may be accomplished by sparging the mixture in a vessel, typically agitated, by contacting the mixture with a gaseous stream in a column that may contain typical distillation packing (e.g., random or structured), by vacuum distillation, or evaporating the lights in an evaporator such as a wiped film evaporator. Typically, steam stripping will be conducted at reduced pressure and at temperatures ranging from about 100° C. to 250° C. The temperature may depend, for example, on the level of vacuum used, with higher vacuum allowing for a lower temperature and allowing for a more efficient and complete separation of volatiles.

In another embodiment, the adsorbent is a water soluble phosphine reagent such as tris hydroxymethyl phosphine (THMP). Catalyst may be separated with a water soluble phosphine through known liquid-liquid extraction mechanisms by decanting the aqueous phase from the organic phase. In other embodiments, the metathesized natural oil product 22 may be contacted with a reactant to deactivate or to extract the catalyst.

In the separation unit 30, in certain embodiments, the metathesized natural oil product 22 is separated into at least two product streams. In one embodiment, the metathesized natural oil product 22 is sent to the separation unit 30, or distillation column, to separate the olefins 32 from the esters 34. In another embodiment, a byproduct stream comprising $C_7$'s and cyclohexadiene may be removed in a side-stream from the separation unit 30. In certain embodiments, the separated olefins 32 may comprise hydrocarbons with carbon numbers up to 24. In certain embodiments, the esters 34 may comprise metathesized glycerides. In other words, the lighter end olefins 32 are preferably separated or distilled overhead for processing into olefin compositions, while the esters 34, comprised mostly of compounds having carboxylic acid/ester functionality, are drawn into a bottoms stream. Based on the quality of the separation, it is possible for some ester compounds to be carried into the overhead olefin stream 32, and it is also possible for some heavier olefin hydrocarbons to be carried into the ester stream 34.

In one embodiment, the olefins 32 may be collected and sold for any number of known uses. In other embodiments, the olefins 32 are further processed in an olefin separation unit 40 and/or hydrogenation unit 50 (where the olefinic bonds are saturated with hydrogen gas 48, as described below). In other embodiments, esters 34 comprising heavier end glycerides and free fatty acids are separated or distilled as a bottoms product for further processing into various products. In certain embodiments, further processing may target the production of the following non-limiting examples: fatty acid methyl esters; biodiesel; 9DA esters, 9UDA esters, and/or 9DDA esters; 9DA, 9UDA, and/or 9DDA; alkali metal salts and alkaline earth metal salts of 9DA, 9UDA, and/or 9DDA; diacids, and/or diesters of the transesterified products; and mixtures thereof. In certain embodiments, further processing may target the production of $C_{15}$-$C_{18}$ fatty acids and/or esters. In other embodiments, further processing may target the production of diacids and/or diesters. In yet other embodiments, further processing may target the production of compounds having molecular weights greater than the molecular weights of stearic acid and/or linolenic acid.

As shown in FIG. 1, regarding the overhead olefins 32 from the separation unit 30, the olefins 32 may be further separated or distilled in the olefin separation unit 40 to separate the stream's various components. In one embodiment, light end olefins 44 consisting of mainly $C_2$-$C_9$ compounds may be distilled into an overhead stream from the olefin separation unit 40. In certain embodiments, the light end olefins 44 are comprised of a majority of $C_3$-$C_8$ hydrocarbon compounds. In other embodiments, heavier olefins having higher carbon numbers may be separated overhead into the light end olefin stream 44 to assist in targeting a specific fuel composition. The light end olefins 44 may be recycled to the metathesis reactor 20, purged from the system for further processing and sold, or a combination of the two. In one embodiment, the light end olefins 44 may be partially purged from the system and partially recycled to the metathesis reactor 20. With regards to the other streams in the olefin separation unit 40, a heavier $C_{16+}$, $C_{18+}$, $C_{20+}$, $C_{22+}$, or $C_{24+}$ compound stream may be separated out as an olefin bottoms stream 46. This olefin bottoms stream 46 may be purged or recycled to the metathesis reactor 20 for further processing, or a combination of the two. In another embodiment, a center-cut olefin stream 42 may be separated out of the olefin distillation unit for further processing. The center-cut olefins 42 may be designed to target a selected carbon number range for a specific fuel composition. As a non-limiting example, a $C_5$-$C_{15}$ distribution may be targeted for further processing into a naphtha-type jet fuel. Alternatively, a $C_8$-$C_{16}$ distribution may be targeted for further processing into a kerosene-type jet fuel. In another embodiment, a $C_8$-$C_{25}$ distribution may be targeted for further processing into a diesel fuel.

In certain embodiments, the olefins 32 may be oligomerized to form poly-alpha-olefins (PAOs) or poly-internal-olefins (PIOs), mineral oil substitutes, and/or biodiesel fuel. The oligomerization reaction may take place after the distillation unit 30 or after the overhead olefin separation unit 40. In certain embodiments, byproducts from the oligomerization reactions may be recycled back to the metathesis reactor 20 for further processing.

As mentioned, in one embodiment, the olefins 32 from the separation unit 30 may be sent directly to the hydrogenation unit 50. In another embodiment, the center-cut olefins 42 from the overhead olefin separation unit 40 may be sent to the hydrogenation unit 50. Hydrogenation may be conducted according to any known method in the art for hydrogenating double bond-containing compounds such as the olefins 32 or center-cut olefins 42. In certain embodiments, in the hydrogenation unit 50, hydrogen gas 48 is reacted with the olefins 32 or center-cut olefins 42 in the presence of a hydrogenation catalyst to produce a hydrogenated product 52.

In some embodiments, the olefins are hydrogenated in the presence of a hydrogenation catalyst comprising nickel, copper, palladium, platinum, molybdenum, iron, ruthenium, osmium, rhodium, or iridium, individually or in combinations thereof. Useful catalyst may be heterogeneous or homogeneous. In some embodiments, the catalysts are supported nickel or sponge nickel type catalysts.

In some embodiments, the hydrogenation catalyst comprises nickel that has been chemically reduced with hydrogen to an active state (i.e., reduced nickel) provided on a support. The support may comprise porous silica (e.g., kieselguhr, infusorial, diatomaceous, or siliceous earth) or alumina. The catalysts are characterized by a high nickel surface area per gram of nickel.

Commercial examples of supported nickel hydrogenation catalysts include those available under the trade designations "NYSOFACT", "NYSOSEL", and "NI 5248 D" (from BASF Catalysts LLC, Iselin, N.J.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

The supported nickel catalysts may be of the type described in U.S. Pat. No. 3,351,566, U.S. Pat. No. 6,846,772, EP 0168091, and EP 0167201, incorporated by reference herein. Hydrogenation may be carried out in a batch or in a continuous process and may be partial hydrogenation or complete hydrogenation. In certain embodiments, the temperature ranges from about 50° C. to about 350° C., about 100° C. to about 300° C., about 150° C. to about 250° C., or about 100° C. to about 150° C. The desired temperature may vary, for example, with hydrogen gas pressure. Typically, a higher gas pressure will require a lower temperature. Hydrogen gas is pumped into the reaction vessel to achieve a desired pressure of $H_2$ gas. In certain embodiments, the $H_2$ gas pressure ranges from about 15 psig (1 atm) to about 3000 psig (204.1 atm), about 15 psig (1 atm) to about 90 psig (6.1 atm), or about 100 psig (6.8 atm) to about 500 psig (34 atm). In certain embodiments, the reaction conditions are "mild," wherein the temperature is approximately between approximately 50° C. and approximately 100° C. and the $H_2$ gas pressure is less than approximately 100 psig. In other embodiments, the temperature is between about 100° C. and about 150° C., and the pressure is between about 100 psig (6.8 atm) and about 500 psig (34 atm). When the desired degree of hydrogenation is reached, the reaction mass is cooled to the desired filtration temperature.

During hydrogenation, the carbon-carbon double bond containing compounds in the olefins are partially to fully saturated by the hydrogen gas 48. In one embodiment, the resulting hydrogenated product 52 includes hydrocarbons with a distribution centered between approximately $C_{10}$ and $C_{12}$ hydrocarbons for naphtha- and kerosene-type jet fuel compositions. In another embodiment, the distribution is centered between approximately $C_{16}$ and $C_{18}$ for a diesel fuel composition.

In certain embodiments, based upon the quality of the hydrogenated product 52 produced in the hydrogenation unit 50, it may be preferable to isomerize the olefin hydrogenated product 52 to assist in targeting of desired fuel properties such as flash point, freeze point, energy density, cetane number, or end point distillation temperature, among other parameters. Isomerization reactions are well-known in the art, as described in U.S. Pat. Nos. 3,150,205; 4,210,771; 5,095,169; and 6,214,764, herein incorporated by reference. In one embodiment, the isomerization reaction at this stage may also crack some of the $C_{15+}$ compounds remaining, which may further assist in producing a fuel composition having compounds within the desired carbon number range, such as 5 to 16 for a jet fuel composition.

In certain embodiments, the isomerization may occur concurrently with the hydrogenation step in the hydrogenation unit 50, thereby targeting a desired fuel product. In other embodiments, the isomerization step may occur before the hydrogenation step (i.e., the olefins 32 or center-cut olefins 42 may be isomerized before the hydrogenation unit 50). In yet other embodiments, it is possible that the isomerization step may be avoided or reduced in scope based upon the selection of low-molecular-weight olefin(s) 14 used in the metathesis reaction.

In certain embodiments, the hydrogenated product 52 comprises approximately 15-25 weight % $C_7$, approximately <5 weight % $C_8$, approximately 20-40 weight % $C_9$, approximately 20-40 weight % $C_{10}$, approximately <5 weight % $C_{11}$, approximately 15-25 weight % $C_{12}$, approximately <5 weight % $C_{13}$, approximately <5 weight % $C_{14}$, approximately <5 weight % $C_{15}$, approximately <1 weight % $C_{16}$, approximately <1 weight % $C_{17}$, and approximately <1 weight % $C_{18}$+. In certain embodiments, the hydrogenated product 52 comprises a heat of combustion of at least approximately 40, 41, 42, 43 or 44 MJ/kg (as measured by ASTM D3338). In certain embodiments, the hydrogenated product 52 contains less than approximately 1 mg sulfur per kg hydrogenated product (as measured by ASTM D5453). In other embodiments, the hydrogenated product 52 comprises a density of approximately 0.70-0.75 (as measured by ASTM D4052). In other embodiments, the hydrogenated product has a final boiling point of approximately 220-240° C. (as measured by ASTM D86).

The hydrogenated product 52 produced from the hydrogenation unit 50 may be used as a fuel composition, non-limiting examples of which include jet, kerosene, or diesel fuel. In certain embodiments, the hydrogenated product 52 may contain byproducts from the hydrogenation, isomerization, and/or metathesis reactions. As shown in FIG. 1, the hydrogenated product 52 may be further processed in a fuel composition separation unit 60, removing any remaining byproducts from the hydrogenated product 52, such as hydrogen gas, water, $C_2$-$C_9$ hydrocarbons, or $C_{15}$+ hydrocarbons, thereby producing a targeted fuel composition. In one embodiment, the hydrogenated product 52 may be separated into the desired fuel $C_9$-$C_{15}$ product 64, and a light-ends $C_2$-$C_9$ fraction 62 and/or a $C_{15}$+ heavy-ends fraction 66. Distillation may be used to separate the fractions. Alternatively, in other embodiments, such as for a naphtha- or kerosene-type jet fuel composition, the heavy ends fraction 66 can be separated from the desired fuel product 64 by cooling the hydrogenated product 52 to approximately −40° C., −47° C., or −65° C. and then removing the solid, heavy ends fraction 66 by techniques known in the art such as filtration, decantation, or centrifugation.

With regard to the esters 34 from the distillation unit 30, in certain embodiments, the esters 34 may be entirely withdrawn as an ester product stream 36 and processed further or sold for its own value, as shown in FIG. 1. As a non-limiting example, the esters 34 may comprise various triglycerides that could be used as a lubricant. Based upon the quality of separation between olefins and esters, the esters 34 may comprise some heavier olefin components carried with the triglycerides. In other embodiments, the esters 34 may be further processed in a biorefinery or another chemical or fuel processing unit known in the art, thereby producing various products such as biodiesel or specialty chemicals that have higher value than that of the triglycerides, for example. Alternatively, in certain embodiments, the esters 34 may be partially withdrawn from the system and sold, with the remainder further processed in the biorefinery or another chemical or fuel processing unit known in the art.

In certain embodiments, the ester stream 34 is sent to a transesterification unit 70. Within the transesterification unit 70, the esters 34 are reacted with at least one alcohol 38 in the presence of a transesterification catalyst. In certain embodiments, the alcohol comprises methanol and/or ethanol. In one embodiment, the transesterification reaction is conducted at approximately 60-70° C. and approximately 1 atm. In certain embodiments, the transesterification catalyst is a homogeneous sodium methoxide catalyst. Varying amounts of catalyst may be used in the reaction, and, in certain embodiments, the transesterification catalyst is present in the amount of approximately 0.5-1.0 weight % of the esters 34.

The transesterification reaction may produce transesterified products 72 including saturated and/or unsaturated fatty acid methyl esters ("FAME"), glycerin, methanol, and/or free fatty acids. In certain embodiments, the transesterified products 72, or a fraction thereof, may comprise a source for biodiesel. In certain embodiments, the transesterified products 72 comprise 9DA esters, 9UDA esters, and/or 9DDA esters. Non-limiting examples of 9DA esters, 9UDA esters and 9DDA esters include methyl 9-decenoate ("9-DAME"), methyl 9-undecenoate ("9-UDAME"), and methyl 9-dodecenoate ("9-DDAME"), respectively. As a non-limiting example, in a transesterification reaction, a 9DA moiety of a metathesized glyceride is removed from the glycerol backbone to form a 9DA ester.

In another embodiment, a glycerin alcohol may be used in the reaction with a glyceride stream. This reaction may produce monoglycerides and/or diglycerides. In certain embodiments, the transesterified products 72 from the transesterification unit 70 can be sent to a liquid-liquid separation unit, wherein the transesterified products 72 (i.e., FAME, free fatty acids, and/or alcohols) are separated from glycerin. Additionally, in certain embodiments, the glycerin byproduct stream may be further processed in a secondary separation unit, wherein the glycerin is removed and any remaining alcohols are recycled back to the transesterification unit 70 for further processing.

In one embodiment, the transesterified products 72 are further processed in a water-washing unit. In this unit, the transesterified products undergo a liquid-liquid extraction when washed with water. Excess alcohol, water, and glycerin are removed from the transesterified products 72. In another embodiment, the water-washing step is followed by a drying unit in which excess water is further removed from the desired mixture of esters (i.e., specialty chemicals). Such specialty chemicals include non-limiting examples such as 9DA, 9UDA, and/or 9DDA, alkali metal salts and alkaline earth metal salts of the preceding, individually or in combinations thereof.

In one embodiment, the specialty chemical (e.g., 9DA) may be further processed in an oligomerization reaction to form a lactone, which may serve as a precursor to a surfactant.

In certain embodiments, the transesterifed products 72 from the transesterification unit 70 or specialty chemicals from the water-washing unit or drying unit are sent to an ester distillation column 80 for further separation of various individual or groups of compounds, as shown in FIG. 1. This separation may include, but is not limited to, the separation of 9DA esters, 9UDA esters, and/or 9DDA esters. In one embodiment, the 9DA ester 82 may be distilled or individually separated from the remaining mixture 84 of transesterified products or specialty chemicals. In certain process conditions, the 9DA ester 82 should be the lightest component in the transesterified product or specialty chemical stream, and come out at the top of the ester distillation column 80. In another embodiment, the remaining mixture 84, or heavier components, of the transesterified products or specialty chemicals may be separated off the bottom end of the column. In certain embodiments, this bottoms stream 84 may potentially be sold as biodiesel.

The 9DA esters, 9UDA esters, and/or 9DDA esters may be further processed after the distillation step in the ester distillation column. In one embodiment, under known operating conditions, the 9DA ester, 9UDA ester, and/or 9DDA ester may then undergo a hydrolysis reaction with water to form 9DA, 9UDA, and/or 9DDA, alkali metal salts and alkaline earth metal salts of the preceding, individually or in combinations thereof.

In certain embodiments, the fatty acid methyl esters from the transesterified products 72 may be reacted with each other to form other specialty chemicals such as dimers.

Multiple, sequential metathesis reaction steps may be employed. For example, the metathesized natural oil product may be made by reacting a natural oil in the presence of a metathesis catalyst to form a first metathesized natural oil product. The first metathesized natural oil product may then be reacted in a self-metathesis reaction to form another metathesized natural oil product. Alternatively, the first metathesized natural oil product may be reacted in a cross-metathesis reaction with a natural oil to form another metathesized natural oil product. Also in the alternative, the transesterified products, the olefins and/or esters may be further metathesized in the presence of a metathesis catalyst. Such multiple and/or sequential metathesis reactions can be performed as many times as needed, and at least one or more times, depending on the processing/compositional requirements as understood by a person skilled in the art. As used herein, a "metathesized natural oil product" may include products that have been once metathesized and/or multiply metathesized. These procedures may be used to form metathesis dimers, metathesis trimers, metathesis tetramers, metathesis pentamers, and higher order metathesis oligomers (e.g., metathesis hexamers, metathesis heptamers, metathesis octamers, metathesis nonamers, metathesis decamers, and higher than metathesis decamers). These procedures can be repeated as many times as desired (for example, from 2 to about 50 times, or from 2 to about 30 times, or from 2 to about 10 times, or from 2 to about 5 times, or from 2 to about 4 times, or 2 or 3 times) to provide the desired metathesis oligomer or polymer which may comprise, for example, from 2 to about 100 bonded groups, or from 2 to about 50, or from 2 to about 30, or from 2 to about 10, or from 2 to about 8, or from 2 to about 6 bonded groups, or from 2 to about 4 bonded groups, or from 2 to about 3 bonded groups. In certain embodiments, it may be desirable to use the metathesized natural products produced by cross metathesis of a natural oil, or blend of natural oils, with a C2-C100 olefin, as the reactant in a self-metathesis reaction to produce another metathesized natural oil product. Alternatively, metathesized natural products produced by cross metathesis of a natural oil, or blend of natural oils, with a C2-C100 olefin can be combined with a natural oil, or blend of natural oils, and further metathesized to produce another metathesized natural oil product.

The metathesized natural oil product may have a number average molecular weight in the range from about 100 g/mol to about 150,000 g/mol, or from about 300 g/mol to about 100,000 g/mol, or from about 300 g/mol to about 70,000 g/mol, or from about 300 g/mol to about 50,000 g/mol, or from about 500 g/mol to about 30,000 g/mol, or from about 700 g/mol to about 10,000 g/mol, or from about 1,000 g/mol to about 5,000 g/mol. The metathesized natural oil product may have a weight average molecular weight in the range from about from about 1,000 g/mol to about 100,000 g/mol, from about 2,500 g/mol to about 50,000 g/mol, from about 4,000 g/mol to about 30,000 g/mol, from about 5,000 g/mol to about 20,000 g/mol, and from about 6,000 g/mol to about 15,000 g/mol. The metathesized natural oil product may have a z-average molecular weight in the range from about from about 5,000 g/mol to about 1,000,000 g/mol, for example from about 7,500 g/mol to about 500,000 g/mol, from about 10,000 g/mol to about 300,000 g/mol, or from about 12,500 g/mol to about 200,000 g/mol. The polydispersity index is calculated by dividing the weight average molecular weight by the number average molecular weight. Polydispersity is a measure of the breadth of the molecular weight distribution of the metathesized natural oil product, and such products generally exhibit a polydispersity index of about 1 to about 20, or from about 2 to about 15. The number average molecular weight, weight average molecular weight, and z-average molecular weight may be determined by gel permeation chromatography (GPC), gas chromatography, gas chromatography mass-spectroscopy, NMR spectroscopy, vapor phase osmometry (VPO), wet analytical techniques such as acid number, base number, saponification number or oxirane number, and the like. In some embodiments, gas chromatography and gas chromatography mass-spectroscopy can be used to analyze the metathesized natural oil product by first transforming the triglycerides to their corresponding methyl esters prior to testing. The extent to which the individual triglyceride molecules have been polymerized can be understood as being directly related to the concentration of diester molecules found in the analyzed fatty acid methyl esters. In some embodiments, the molecular weight of the metathesized natural oil product can be increased by transesterifying the metathesized natural oil product with diesters. In some embodiments, the molecular weight of the metathesized natural oil product can be increased by esterifying the metathesized natural oil product with diacids. In certain embodiments, the metathesized natural oil product has a viscosity between about 1 centipoise (cP) and about 10,000 centipoise (cP), between about 30 centipoise (cP) and about 5000 cP, between about 50 cP and about 3000 cP, and from between about 80 cP and about 1500 cP.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen, individually or in combinations thereof.

In certain embodiments, the metathesis catalyst is dissolved in a solvent prior to conducting the metathesis reaction. In certain embodiments, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In one particular embodiment, the solvent comprises toluene. The metathesis reaction temperature may be a rate-controlling variable where the temperature is selected to provide a desired product at an acceptable rate. In certain embodiments, the metathesis reaction temperature is greater than about −40° C., greater than about −20° C., greater than about 0° C., or greater than about 10° C. In certain embodiments, the metathesis reaction temperature is less than about 150° C., or less than about 120° C. In one embodiment, the metathesis reaction temperature is between about 10° C. and about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 0.1 atm (10 kPa), in some embodiments greater than about 0.3 atm (30 kPa), or greater than about 1 atm (100 kPa). Typically, the reaction pressure is no more than about 70 atm (7000 kPa), in some embodiments no more than about 30 atm (3000 kPa). A non-limiting exemplary pressure range for the metathesis reaction is from about 1 atm (100 kPa) to about 30 atm (3000 kPa). In certain embodiments it may be desirable to run the metathesis reactions under an atmosphere of reduced pressure. Conditions of reduced pressure or vacuum may be used to remove olefins as they are generated in a metathesis reaction, thereby driving the metathesis equilibrium towards the formation of less volatile products. In the case of a self-metathesis of a natural oil, reduced pressure can be used to remove C12 or lighter olefins including, but not limited to, hexene, nonene, and dodecene, as well as byproducts including, but not limited to cyclohexadiene and benzene as the metathesis reaction proceeds. The removal of these species can be used as a means to drive the reaction towards the formation of diester groups and cross linked triglycerides.

The metathesized natural oil compositions described herein may be utilized independently and/or incorporated into various formulations and used as functional ingredients in dimethicone replacements, laundry detergents, fabric softeners, personal care applications, such as emollients, hair fixative polymers, rheology modifiers, specialty conditioning polymers, surfactants, UV absorbers, solvents, humectants, occlusives, film formers, or as end use personal care applications, such as cosmetics, lip balms, lipsticks, hair dressings, sun care products, moisturizer, fragrance sticks, perfume carriers, skin feel agents, shampoos/conditioners, bar soaps, hand soaps/washes, bubble baths, body washes, facial cleansers, shower gels, wipes, baby cleansing products, creams/lotions, and antiperspirants/deodorants.

The metathesized natural oil compositions described herein may also be incorporated into various formulations and used as functional ingredients in lubricants, functional fluids, fuels and fuel additives, additives for such lubricants, functional fluids and fuels, plasticizers, asphalt additives, friction reducing agents, antistatic agents in the textile and plastics industries, flotation agents, gelling agents, epoxy curing agents, corrosion inhibitors, pigment wetting agents, in cleaning compositions, plastics, coatings, adhesives, skin feel agents, film formers, rheological modifiers, release agents, conditioners dispersants, hydrotropes, industrial and institutional cleaning products, oil field applications, gypsum foamers, sealants, agricultural formulations, enhanced oil recovery compositions, solvent products, gypsum products, gels, semi-solids, detergents, heavy duty liquid detergents (HDL), light duty liquid detergents (LDL), liquid detergent softeners, antistat formulations, dryer softeners, hard surface cleaners (HSC) for household, autodishes, rinse aids, laundry additives, carpet cleaners, softergents, single rinse fabric softeners, I&I laundry, oven cleaners, car washes, transportation cleaners, drain cleaners, defoamers, anti-foamers, foam boosters, anti-dust/dust repellants, industrial cleaners, institutional cleaners, janitorial cleaners, glass cleaners, graffiti removers, concrete cleaners, metal/machine parts cleaners, pesticides, agricultural formulations and food service cleaners, plasticizers, asphalt additives and emulsifiers, friction reducing agents, film formers, rheological modifiers, biocides, biocide potentiators, release agents, household cleaning products, including liquid and powdered laundry detergents, liquid and sheet fabric softeners, hard soft surface cleaners, sanitizers and disinfectants, and industrial cleaning products, emulsion polymerization, including processes for the manufacture of latex and for use as surfactants as wetting agents, and in agriculture applications as formulation inerts in pesticide applications or as adjuvants used in conjunction with the delivery of pesticides including agricultural crop protection turf and ornamental, home and garden, and professional applications, and institutional cleaning products, oil field applications, including oil and gas transport, production, stimulation and drilling chemicals and reservoir conformance and enhancement, organoclays for drilling muds, specialty foamers for foam control or dispersancy in the manufacturing process of gypsum, cement wall board, concrete additives and firefighting foams, paints and coalescing agents, paint thickeners, or other applications requiring cold tolerance performance or winterization (e.g., applications requiring cold weather performance without the inclusion of additional volatile components).

The following examples and data merely illustrate the invention. It is to be understood that various modifications thereof will become apparent to those skilled in the art upon reading the specification. Therefore, it is to be understood that the invention disclosed herein includes any such modifications that may fall within the scope of the appended claims.

EXAMPLES

Multiple Metathesis Example

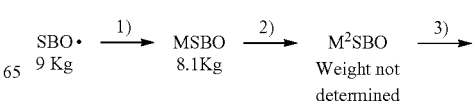

19
-continued

M³SBO →4) M⁴SBO
Weight not determined    6.1 Kg 1) 9 ppm C827/toluene, 65° C.
   High vacuum, 180 min RXN time
   THMP treatment/Filtration
   Removal of lights
   61% conversion by GC
2) 50 ppm C827/toluene, 70° C.
   High vacuum, 180 min RXN time
   Removal of lights up to 247° C.
   65% conversion by GC
3) 1.7 ppm C827/toluene, 70° C.
   High vacuum, 45 min RXN time
   Removal of lights up to 136° C.
   No GC analysis
   30 r/min at 70° C. 1350 cP (S63)
3) 2 ppm C827/toluene, 70° C.
   High vacuum, 45 min RXN time
   No GC analysis
   Too viscous to measure Physical Properties of Metathesized Soybean Oil
(Samples A, B and C)

SAMPLE A

| Kinematic Viscosity @ 40° C. (ASTM D445, in cSt) | Kinematic Viscosity @ 100° C. (ASTM D445, in cSt) | Viscosity Index | Noack Volatility (ASTM D5800) | Pour Point (ASTM D97, in ° C.) |
|---|---|---|---|---|
| 246 | 40 | 219 | 8.3 wt % | 6 |

20

SAMPLE B

| Brookfield Viscosity (in cP) | Flash Point (ASTM D93, in ° C.) | Pour Point (ASTM D97, in ° C.) |
|---|---|---|
| 295 | 177 | 3 |

SAMPLE C

| | | |
|---|---|---|
| Once metathesized (1x) | unstripped | 135 cP |
| Once metathesized (1x) | stripped at 150° C. | 262.5 cP |
| Once metathesized (1x) | stripped at 200° C. | 305 cP |
| Twice metathesized (2x) | unstripped | 392.5 cP |
| Twice metathesized (2x) | stripped at 150° C. | 567.5 cP |
| Twice metathesized (2x) | stripped at 200° C. | 650 cP |

Viscosity measurements for Sample C were performed at 40° C.

Figure 2:
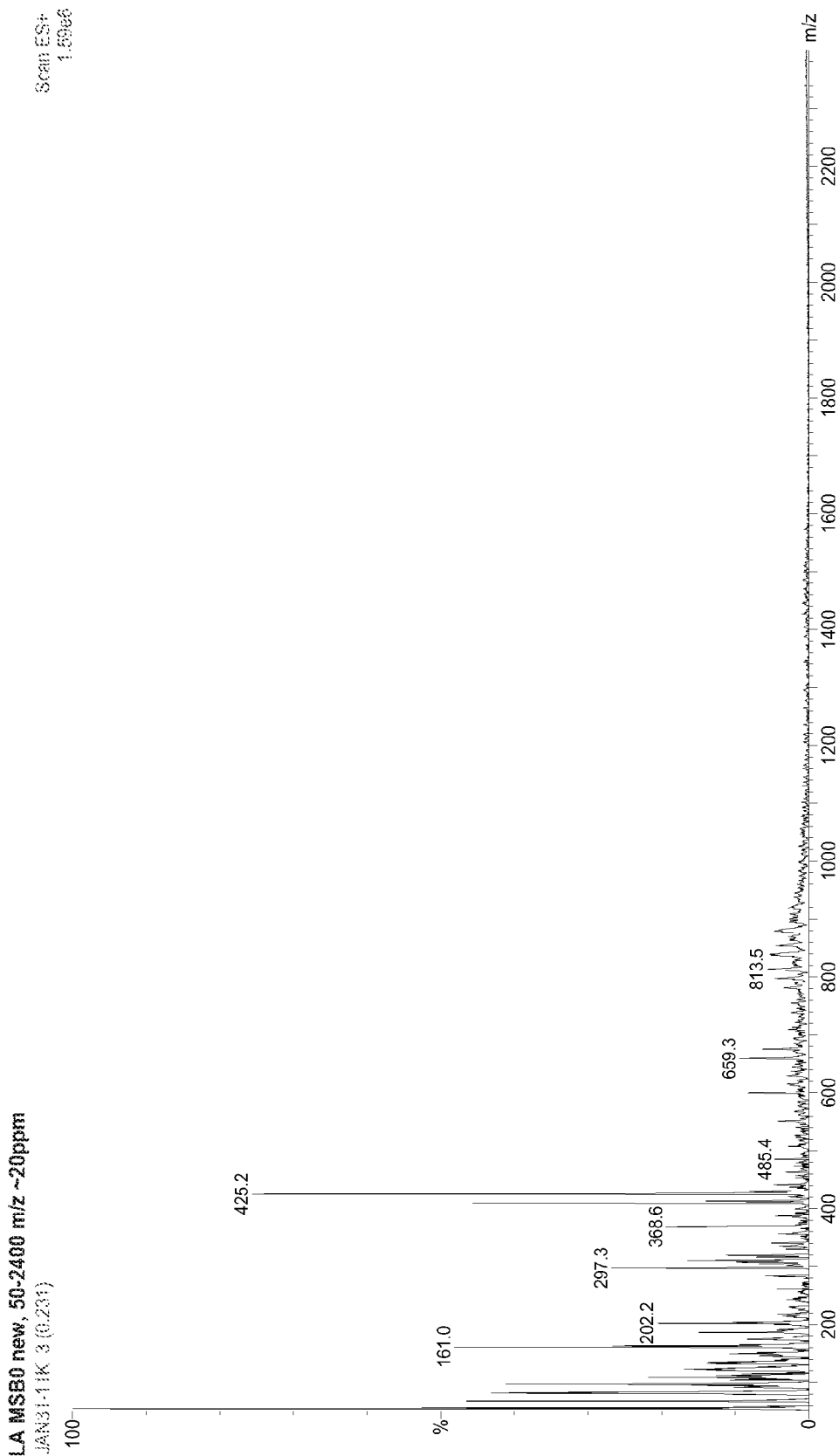
FIG. 2 depicts a mass spectrum of a metathesized natural oil product.
Figure 3:
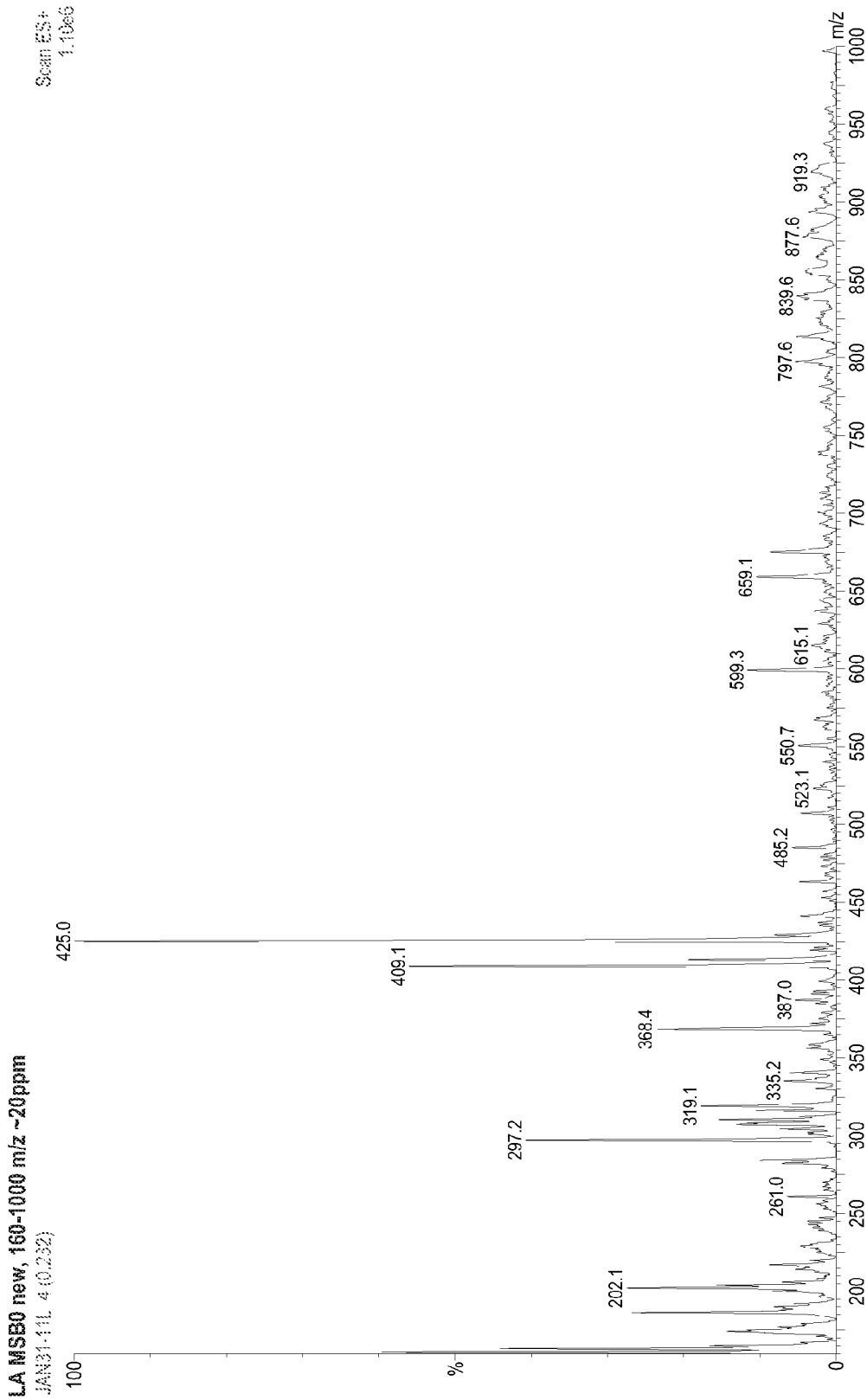
FIG. 3 depicts a mass spectrum of a metathesized natural oil product.

Various Compositional Fractions of MSBO.
Reference FIG. 2 and FIG. 3 for Mass Spectra Analyses 1. peak at 368

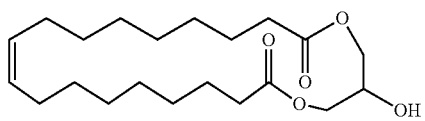

(Z)-3-hydroxy-1,5-dioxacyclotricos-14-ene-6,23-dione
Chemical Formula: $C_{21}H_{36}O_5$
Molecular Weight: 368.51

2. peak at 409

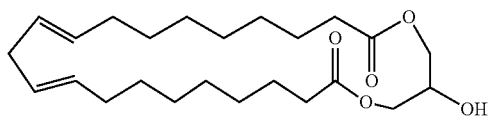

(14E,17E)-3-hydroxy-1,5-dioxacyclohexacosa-14,17-diene-6,26-dione
Chemical Formula: $C_{24}H_{40}O_5$
Molecular Weight: 408.57

3. Peak at 659

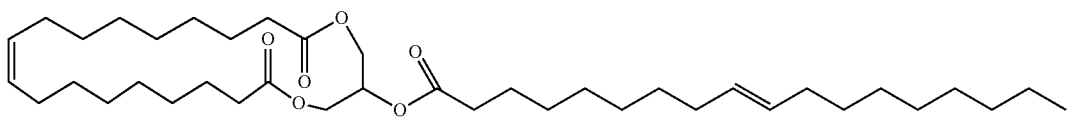

(E)-((Z)-6,23-dioxo-1,5-dioxacyclotricos-14-en-3-yl)
octadec-9-enoate
Chemical Formula: $C_{39}H_{68}O_6$
Molecular Weight: 632.95
M + Na (23) = 655.95
M + K (39) = 671.95

4. peak at 675

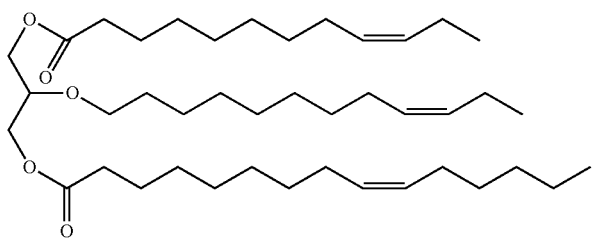

Chemical Formula: $C_{42}H_{74}O_6$
Molecular Weight: 675.03

5. peak at 797

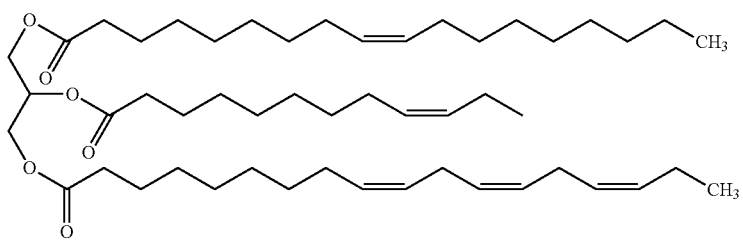

Chemical Formula: $C_{51}H_{88}O_6$
Molecular Weight: 797.24

6. peak at 877.6

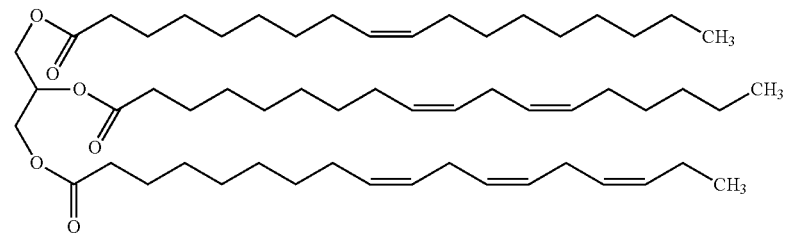

Chemical Formula: $C_{57}H_{98}O_6$
Molecular Weight: 879.38

7. peak ~919

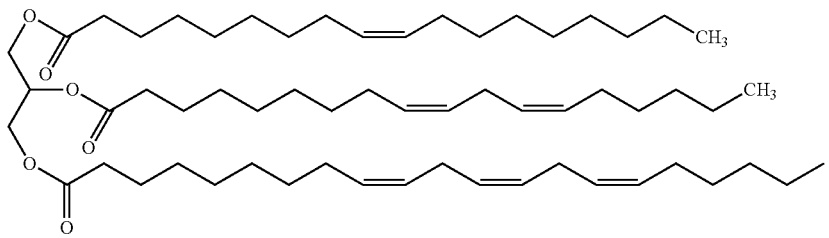

Chemical Formula: $C_{60}H_{104}O_6$
Molecular Weight: 921.46

Figure 4:
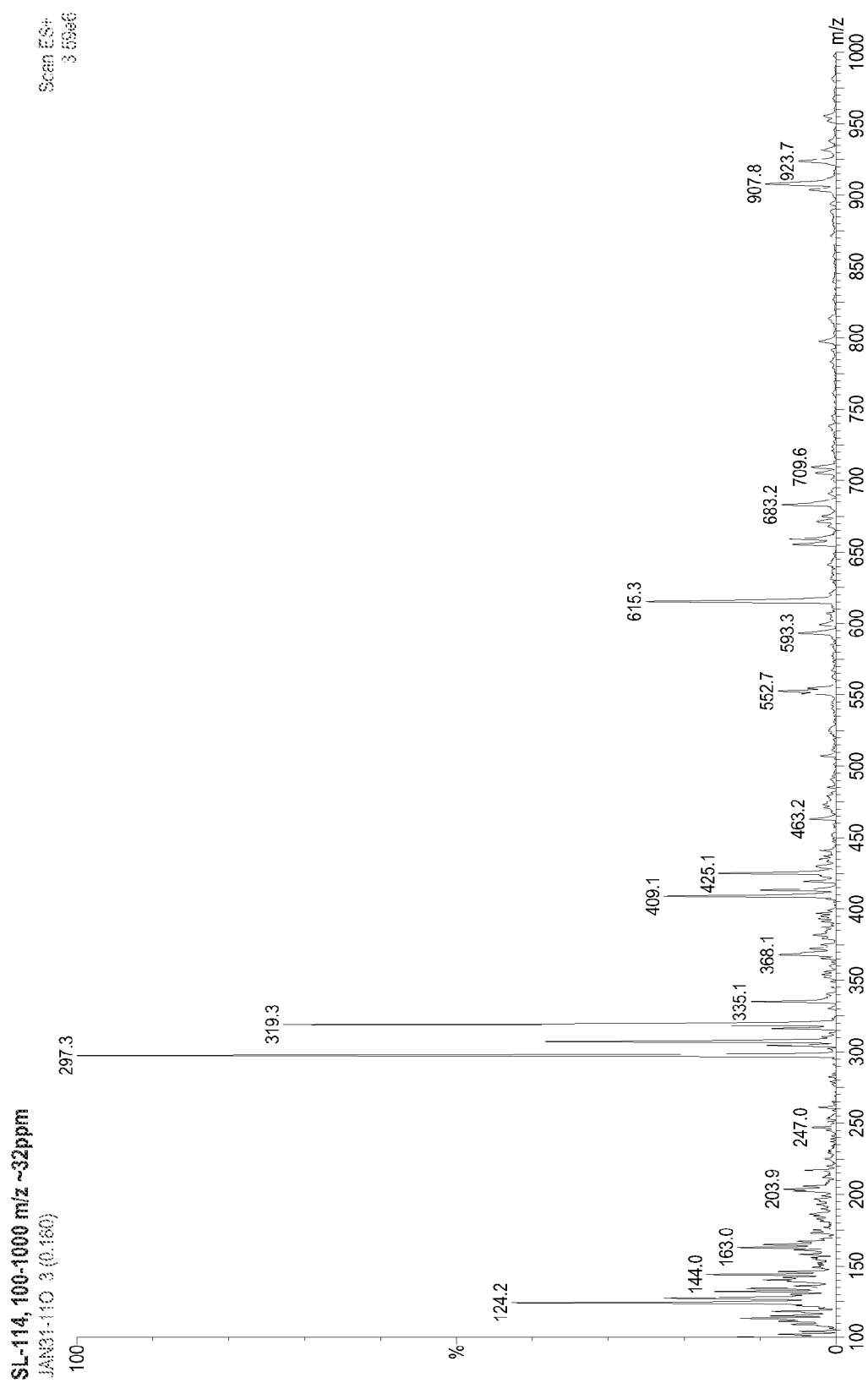
FIG. 4 depicts a mass spectrum of a metathesized natural oil product.
Figure 5:
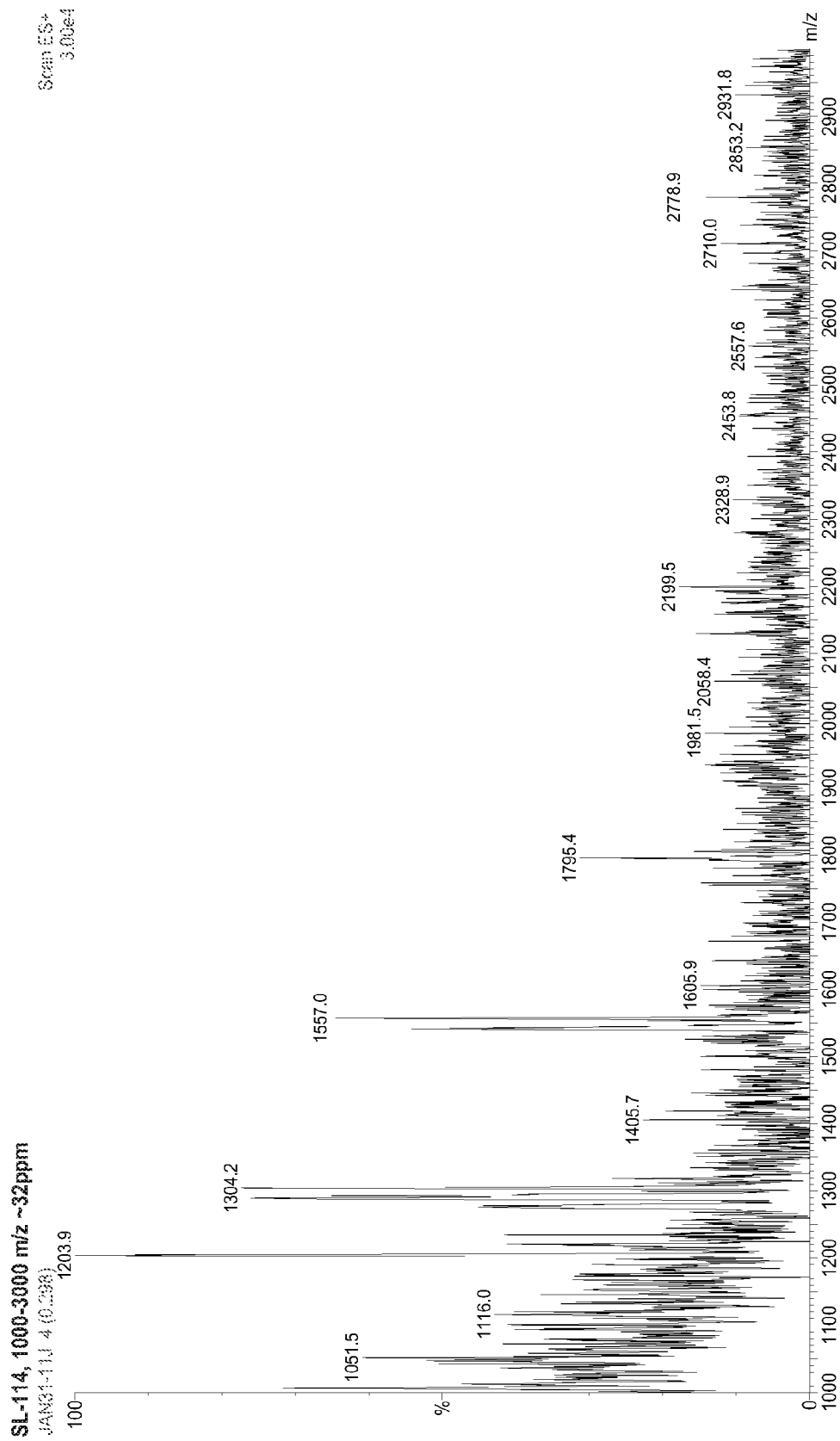
FIG. 5 depicts a mass spectrum of a metathesized natural oil product.

Metathesis Reaction of Triolein (Oleyl Triglyceride) with Grubbs $2^{nd}$ Generation Catalyst 1 gram Triolein in a flask was heated to 45° C. under $N_2$ protection. 0.01 gram Catalyst was added. They reaction was kept at 45° C. for 16 hours and quenched with ethyl vinyl ether. The mixture was dissolved in Ethyl acetate and filtered through celite. The MS of resultant samples was tested on a triple quadrupole mass spectrometer with electrospray ionization source for Micromass Quattro LC. Reference FIG. 4 and FIG. 5 for mass spectra analyses.

1. peak at 907

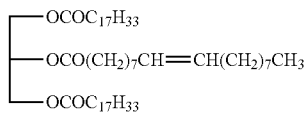

Chemical Formula: $C_{57}H_{104}O_6$
Molecular Weight: 885.43
M + Na (23) = 908
M + K (39) = 924

2. peak at 409

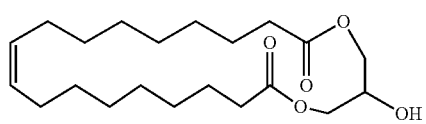

(Z)-3-hydroxy-1,5-dioxacyclotricos-
14-ene-6,23-dione
Chemical Formula: $C_{21}H_{36}O_5$
Molecular Weight: 368.51
M + Na (23) = 391.51
M + K (39) = 407.51

3. Peak at ~655

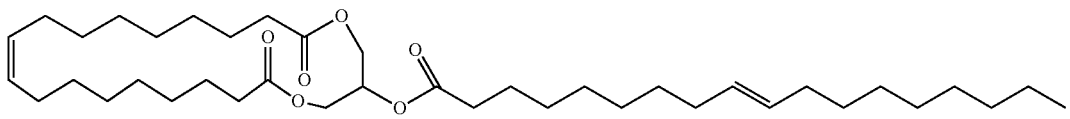

(E)-((Z)-6,23-dioxo-1,5-dioxacyclotricos-14-en-3-yl)
octadec-9-enoate
Chemical Formula: $C_{39}H_{68}O_6$
Molecular Weight: 632.95
M + Na (23) = 655.95
M + K (39) = 671.95

4. Peak at 1051

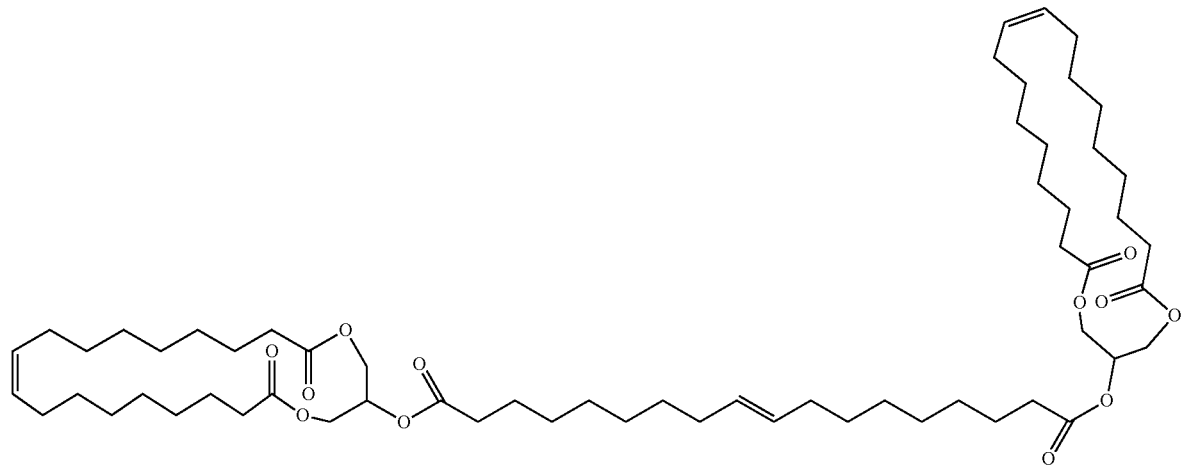

(E)-bis((Z)-6,23-dioxo-1,5-dioxacyclotricos-14-en-3-yl) octadec-9-enedioate
Chemical Formula: $C_{60}H_{100}O_{12}$
Molecular Weight: 1013.43
M + Na (23) = 1036
M + K (39) = 1052

5. Peak at 1557

Dimer

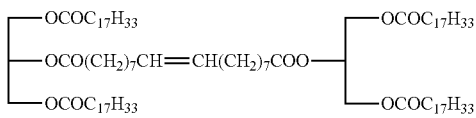

Chemical Formula: $C_{96}H_{172}O_{12}$
Molecular Weight: 1518.39
M + Na (23) = 1541
M + K (39) = 1557

6. Peak at 2199

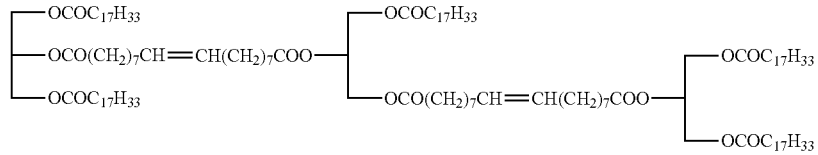

Chemical Formula: $C_{135}H_{240}O_{18}$
Molecular Weight: 2151.34
M + Na (23) = 2174
M + K (39) = 2190

7. Peak at ~1300

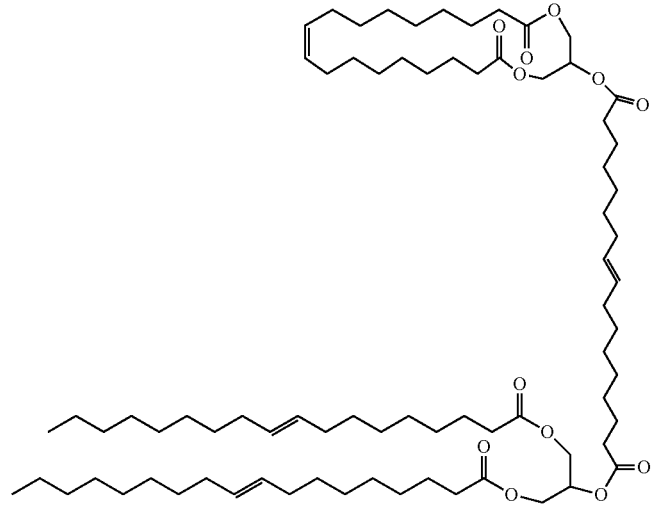

(E)-17-(1,3-bis((E)-octadec-9-enoyloxy)propan-2-yl)
1-((Z)-6,23-dioxo-1,5-dioxacyclotricos-14-en-3-yl) heptadec-8-enedioate
Chemical Formula: $C_{77}H_{134}O_{12}$
Molecular Weight: 1251.88
M + Na (23) = 1274
M + K (39) = 1290.88

Metathesis of Canola Oil to Generate FAME and Diesters

Refined bleached and deodorized canola oil (170 g) was loaded into a 250 ml 2-neck round bottom flask with a magnetic stir bar. The top joint of the flask was fitted with a 320 mm cold coil condenser fed by a chiller circulator set to 15° C. To the top of the condenser was fitted a hose adapter connected to an oil bubbler via Tygon tubing. The side arm neck was fitted with a rubber septum through which was fed a needle type thermocouple and an 18 gauge stainless steel needle for the purpose of supplying the flask with a nitrogen source. The oil was heated, with magnetic stirring, for 2 hr at 200° C. while being sparged with dry nitrogen. After 2 hr, the oil was allowed to cool to 70° C., before adding the metathesis catalyst. The catalyst (Materia C827) was added via canola oil slurry through the top joint of the flask with a nitrogen sweep being maintained throughout the slurry addition. At this time the coil condenser was replaced. The reaction mixture was sparged with nitrogen an additional five minutes, to insure an inert atmosphere, before the nitrogen supply was closed. Metathesis was carried out for 3 hr at 70° C., with no nitrogen sweep, before raising the temperature of the reaction mixture to 100° C. for the purpose of deactivating the catalyst. Following 1 hr at 100° C., the reaction mixture was allowed to cool to ambient temperature overnight, under a slow nitrogen sweep.

The next day, the rubber septum was exchanged for PTFE thermocouple adapter, and the coil condenser was exchanged for a short path distillation head with jacketed condenser equipped with a 100 ml receiving flask. The reaction mixture was stripped to a pot temperature of 250° C. at a pressure of 300 mTorr for 4.5 hr. Stripping resulted in the removal of 17.4 wt. % lights and yielded a slightly burnt looking oil product. Brookfield viscosity of the final product was measured as 710 cP at 40° C. Conversion of the product to its corresponding fatty acid methyl esters was accomplished prior to analysis by gas chromatography. The resulting mixture of fatty acid methyl esters was found to contain 27 wt. % diesters as shown by gas chromatography.

Data Set #1 on Metathesized Natural Oil Compositions

In the Data Sets below, Mn refers to number average molecular weight, Mw refers to weight average molecular weight, Mz refers to z average molecular weight, PDI refers to polydispersity index, TGA refers to thermogravimetric analysis, and IV refers to intrinsic viscosity. Also, MSBO refers to metathesized soybean oil, MCO refers to metathesized canola oil, and 2× refers to twice metathesized.

| Notebook # | Product | Description | Diester Content | Mn | Mw | Mz | PDI | Viscosity @ 40 C | TGA | IV |
|---|---|---|---|---|---|---|---|---|---|---|
| 1033-96-5 | MSBO | Stripped, filtered | 16.85 | 2461 | 6946 | 12987 | 2.82 | 281 cP | n/a | n/a |
| 1064-6-4 | 2XMSBO | 2XMSBO Stripped at 200° C. | 22.17 | 3034 | 12827 | 38689 | 4.23 | 650 cP | n/a | 108.54 |
| 1106-94-C | MCBO | Super gel | 31.72 | 2653 | 27098 | 121316 | 10.21 | Too Viscous to measure | n/a | n/a |
| 1106-96-D | MCO | n/a | n/a | 2982 | 11142 | 32490 | 3.74 | 700 cP | n/a | 77.52 |
| 1106-98-D | MCO | n/a | n/a | 2844 | 10603 | 29450 | 3.73 | 750 cP | n/a | 91.17 |
| 1129-12-2 | 2XMSBO | Stripped at 200° C. | 25.06 | 2336 | 9693 | 28181 | 4.15 | 642 cP | 2.37% | 85.62 |
| 1129-13-1 | MSBO | Stripped at 200° C. | 24.26 | 2363 | 7363 | 18648 | 3.11 | 474 cP | n/a | n/a |
| 1129-13-2 | 2XMSBO | Stripped at 200° C. | n/a | n/a | n/a | n/a | n/a | n/a | n/a | n/a |
| BB9004 | MSBO | Stripped at 150° C. | 26.73 | 3393 | 20608 | 63294 | 6.07 | 1525 cP | n/a | n/a |
| BB9012 | MSBO | Stripped at 150° C. | 23.48 | 2933 | 15175 | 44975 | 5.17 | 990 cP | n/a | n/a |
| BB9013 | MSBO | Stripped at 150° C. | 23.29 | 3007 | 15899 | 47980 | 5.29 | 1215 cP | n/a | n/a |
| BB9014 | 2XMSBO | 2XMSBO Stripped at 150° C. | 23.17 | 2779 | 13302 | 45017 | 4.79 | 590 cP | n/a | 112.50 |
| BB9015 | 2XMSBO | 2XMSBO Stripped at 200° C. | 23.03 | 2691 | 12142 | 41782 | 4.51 | 635 cP | n/a | 113.88 |

Data Set #2 on Metathesized Natural Oil Compositions

| | Sample no. | Feedstock | Stripping temp, ° C. | Viscosity 40° C. (cP) | Mn | Mw | Mz | PDI |
|---|---|---|---|---|---|---|---|---|
| Once metathesized (1X) | BB9028 | soy oil | 200 | 305 | NA | NA | NA | NA |
| Once metathesized (1X) | BB9040 | soy oil | 200 | 285 | 2397 | 5913 | 13273 | 2.5 |
| Twice metathesized (2X) | BB9035 | BB9028 | 150 | 2930 | 2594 | 31089 | 110887 | 12.0 |
| Twice metathesized (2X) | BB9039 | BB9028 | 200 | 3244 | 2750 | 31235 | 105716 | 11.4 |
| Twice metathesized (2X) | BB9047A | BB9040 | 150 | 2660 | NA | NA | NA | NA |
| Twice metathesized (2X) | BB9047B | BB9040 | 200 | 3050 | 2900 | 30819 | 102295 | 10.6 |

NOTE:
All catalyst loading = 38-42 ppm. All reaction temp = 70° C.

Data Set #3 on Metathesized Natural Oil Compositions

| Sample no. | Feedstock | Stripping temp, ° C. | Viscosity 100° C. (cSt) |
|---|---|---|---|
| Once metathesized (1X) BB8089 | Canola oil | 200 | 88.4 |
| Once metathesized (1X) BB8087 | Canola oil | 200 | 83.7 |
| Once metathesized (1X) BB8092B | Canola oil | 200 | 82.3 |
| Twice metathesized (2X) BB8092D | BB8092B | 200 | 549.9 |

We claim:

1. A metathesized natural oil composition comprising one or more metathesis oligomers, which are formed from the self-metathesis of natural oil glycerides,
wherein the natural oil glycerides comprise metathesized natural oil glycerides, which are formed by the cross-metathesis of a natural oil glycerides with $C_2$-$C_6$ low-molecular-weight olefins, and
wherein the one or more metathesis oligomers have a weight average molecular weight in the range from 2,500 g/mol to 50,000 g/mol.

2. The metathesized natural oil composition of claim 1, wherein the one or more metathesis oligomers have a weight average molecular weight in the range from 2,500 g/mol to 50,000 g/mol.

3. The metathesized natural oil composition of claim 1, wherein the $C_2$-$C_6$ low-molecular-weight olefins are selected from the group consisting of ethylene, propylene, 1-butene, 2-butene, and isobutene.

* * * * *